United States Patent
DeMan et al.

(10) Patent No.: US 8,571,287 B2
(45) Date of Patent: Oct. 29, 2013

(54) SYSTEM AND METHOD FOR ITERATIVE IMAGE RECONSTRUCTION

(75) Inventors: Bruno DeMan, Clifton Park, NY (US); Samit Kumar Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 1626 days.

(21) Appl. No.: 11/474,613

(22) Filed: Jun. 26, 2006

(65) Prior Publication Data

US 2007/0297656 A1 Dec. 27, 2007

(51) Int. Cl.
*G06K 9/00* (2006.01)
(52) U.S. Cl.
USPC .......................................... 382/131; 600/407
(58) Field of Classification Search
USPC .......................................... 382/131; 600/407
See application file for complete search history.

(56) References Cited

U.S. PATENT DOCUMENTS

| | | | | |
|---|---|---|---|---|
| 6,185,320 B1 * | 2/2001 | Bick et al. | ...................... | 382/132 |
| 6,724,856 B2 | 4/2004 | DeMan et al. | | |
| 2003/0156746 A1 * | 8/2003 | Bissell et al. | ................. | 382/128 |
| 2006/0064007 A1 * | 3/2006 | Comaniciu et al. | ........... | 600/416 |
| 2007/0086678 A1 * | 4/2007 | Chefd'hotel et al. | ......... | 382/294 |

OTHER PUBLICATIONS

Bruck et al., "Digital Image Correlation Using Newton-Raphson Method of Partial Differential Correction", Sep. 1989, vol. 29, Issue 3, Experimental Mechanics, 261-267.*
Bouman et al., "A Unified Approach to Statistical Tomography Using Coordinate Descent Optimization", 1996, IEEE Transactions on Image Processing, vol. 5, No. 3, 480-492.*
Pratt et al., "Gauss-Newton and full Newton methods in frequency-space seismic waveform inversion", May 1998, Geophysical Journal International, vol. 133, Issue 2, pp. 341-362.*
Chen, Pei et al. Three-dimensional multi-resolution statistical reconstruction for tomosynthesis. *Biomedical Imaging: Macro to Nano, 2004.* IEEE International Symposium. Apr. 15-18, 2004, pp. 559-562, vol. 1.
DeMan, Bruno et al. Distance-driven projection and backprojection. *IEEE Nuclear Science Symposium Conference Record, 2002.* Nov. 10-16, 2002, pp. 1477-1480, vol. 3.
DeMan, Bruno et al. Distance-driven projection and backprojection in three dimensions. *Physics in Medical Biology.* May 19, 2004, pp. 2463-2475, vol. 49.
DeMan, Bruno et al. Presentation: Distance-driven projection and backprojection for group-coordinate and single-coordinate descent. Imaging 2006. Jun. 27, 2006. Stockholm, Germany.
DeMan, Bruno et al. Publication: Generalized Geman prior for iterative reconstruction. International Congress of Medical Physics. Sep. 14-17, 2005. Nuremberg, Germany.
DeMan, Bruno et al. Presentation: Generalized Geman prior for iterative reconstruction. International Congress of Medical Physics. Sep. 14-17, 2005. Nuremberg, Germany.
Fessler, Jeffrey A. et al. Grouped-Coordinate Ascent Algorithms for Penalized-Likelihood Image Reconstruction. *IEEE Transactions on Medical Imaging.* Apr. 1997, pp. 166-175, vol. 16, No. 2.

* cited by examiner

*Primary Examiner* — David Zarka
*Assistant Examiner* — Katrina Fujita
(74) *Attorney, Agent, or Firm* — Marie-Claire B. Maple

(57) ABSTRACT

Methods are provided for iteratively reconstructing an image signal to generate a reconstructed image signal. In one embodiment, sub-iterations of each iteration are performed on pixel subsets. The pixel subsets may be composed of pixels neighboring or spatially separated pixel. In a further embodiment, each iteration is performed at a different resolution. Systems and computer routines for processing image data iteratively in accordance with these techniques are also provided.

22 Claims, 4 Drawing Sheets

SYSTEM AND METHOD FOR ITERATIVE IMAGE RECONSTRUCTION

BACKGROUND

The invention relates generally to imaging techniques and, more specifically, to the iterative reconstruction of images acquired by non-invasive tomographic imaging modalities.

Non-invasive imaging broadly encompasses techniques for generating images of the internal structures or regions of a person that are otherwise inaccessible for visual inspection. One of the best known uses of non-invasive imaging is in the medical arts where these techniques are used to generate images of organs and/or bones inside a patient which would otherwise not be visible. Other well known uses are in the field of non-destructive testing, such as for security and package screening or for quality control of manufacturing processes. Example of such non-invasive imaging modalities include X-ray based techniques, such as computed tomography (CT), as well as nuclear based technique, such as positron emission tomography (PET) and single photon emission computed tomography (SPECT).

With regard to CT imaging techniques, CT scanners operate by projecting fan shaped or cone shaped X-rays from an X-ray source. The X-ray source emits X-rays at numerous angles relative to an object being imaged, such as a patient, which attenuates the X-rays as they pass through. The attenuated X-rays are detected by a set of detector elements, which produce signals representing the attenuation of the incident X-rays. The signals are processed and reconstructed to form images which may be evaluated themselves or which may be associated to form a volume rendering or other representation of the imaged region. In a medical context, pathologies or other structures of interest may then be located or identified from the reconstructed images or rendered volume.

CT reconstruction is usually performed using direct reconstruction techniques based on mathematical ideals that are not typically observed in practice. One side effect of the failure of the mathematical ideals to correspond to actual practice is that noise and resolution performance for a given X-ray dose is typically not optimized using direct reconstruction techniques.

Iterative reconstruction techniques overcome these problems by employing various mathematical models, such as noise and system models, to account for deviations from the mathematical ideals. Iterative reconstruction techniques repeatedly apply respective forward and backward projection models to generate an image that best fits the image measurements according to an appropriate objective function. In this manner, iterative reconstruction algorithms may provide improved image quality and/or reduced X-ray dosage. In addition, iterative reconstruction algorithms may provide other benefits, such as reduction of metal artifacts in reconstructed images.

However, iterative reconstruction algorithms require significantly more computation than conventional, i.e., direct, reconstruction methods and have thus far been impractical for mainstream CT applications. In particular, iterative reconstruction algorithms undergo many iterations to generate each image, i.e., to converge. Further, each iteration employs two or more computationally intensive projection and backprojection operations. As a result, iterative reconstruction algorithms may require an order of magnitude or more computational effort than a direct reconstruction technique to construct a single image. Consequently, iterative reconstruction approaches are typically much slower than comparable direct reconstruction approaches.

BRIEF DESCRIPTION

A method is provided for processing image data. The method includes the step of providing an image. A respective Hessian matrix corresponding to each subset of pixels is directly inverted such that the pixels of each subset are simultaneously optimized with regard to a cost function. Corresponding system and computer-readable media claims are also provided.

A further method for processing image data is provided. The method includes the step of providing an image. The image is iteratively processed such that each iteration processes the image at a different resolution. Each iteration comprises two or more subiterations. Each subiteration corresponds to the processing of a subset of the pixels at the corresponding resolution. Corresponding system and computer-readable media claims are also provided.

An additional method for processing image data is provided. The method includes the step of providing an image comprising a plurality of pixels. An update is determined for each subset of two or more subsets of the plurality of pixels. An optimized update is generated based upon the aggregated updates. Corresponding system and computer-readable media claims are also provided.

An additional method for processing image data is provided. The method includes the step of providing an image comprising a plurality of pixels. At least one subset of the plurality of pixels is processed by at least one of distance driven projection or backprojection. Corresponding system and computer-readable media claims are also provided.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
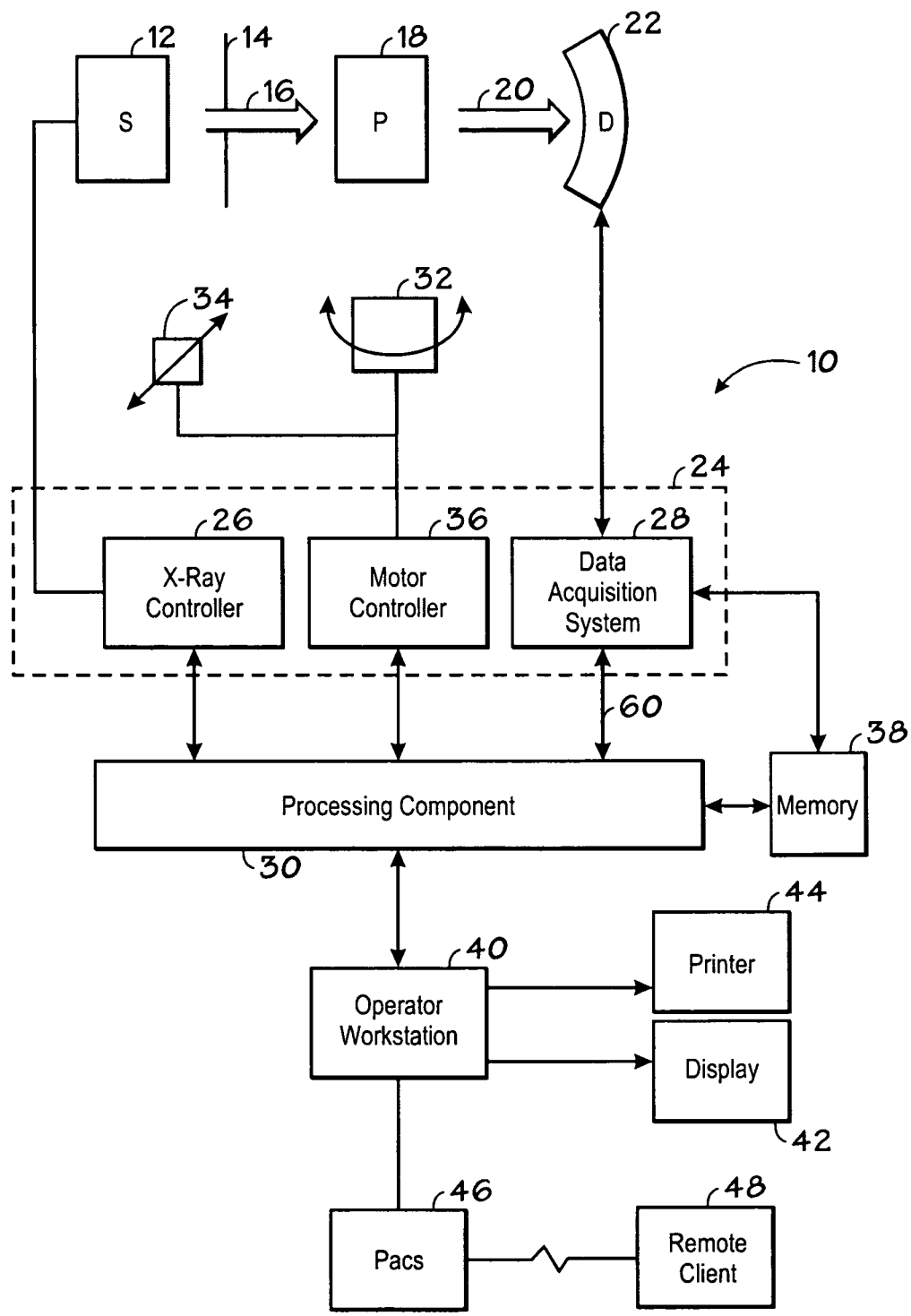
FIG. 1 is a diagrammatical view of an exemplary imaging system in the form of a CT imaging system for use in producing images in accordance with aspects of the present technique.

FIG. 1 illustrates diagrammatically an imaging system 10 for acquiring and processing projection data to produce reconstructed images. In the illustrated embodiment, system 10 is a computed tomography (CT) system designed both to acquire original image data, and to process the image data for display and analysis in accordance with the present technique. In other embodiments, the imaging system may be a positron emission tomography (PET) system, a single photon emission computed tomography (SPECT) system, or any other imaging system suitable for generating tomographic images. The depicted system 10 is configured to employ iterative reconstruction techniques in the processing of acquired or saved projection data to reconstruct medically useful images in accordance with the present technique. In the embodiment illustrated in FIG. 1, imaging system 10 includes a source of X-ray radiation 12 positioned adjacent to a collimator 14. In one exemplary embodiment the X-ray source 12 is an X-ray tube. In other embodiments the X-ray source 12 may be a distributed X-ray source, such as a solid-state or thermionic X-ray source, or may be other sources of X-ray radiation suitable for the acquisition of medical images.

The collimator 14 permits X-rays 16 to pass into a region in which an object, such as a subject of interest 18, is positioned. A portion of the X-ray radiation 20 passes through or around the subject and impacts a detector array, represented generally at reference numeral 22. Detector elements of the array produce electrical signals that represent the intensity of the incident X-rays 20. These signals are acquired and processed to reconstruct images of the features within the subject 18.

Source 12 is controlled by a system controller 24, which furnishes both power, and control signals for CT examination sequences. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which commands acquisition of the signals generated in the detector 22. In the depicted embodiment, the system controller 24 acquires the signals generated by the detector using a data acquisition system 28. In this exemplary embodiment, the detector 22 is coupled to the system controller 24, and more particularly to the data acquisition system 28. The data acquisition system 28 receives data collected by readout electronics of the detector 22. The data acquisition system 28 typically receives sampled analog signals from the detector 22 and converts the data to digital signals for subsequent processing by a processor 30 discussed below. The system controller 24 may also execute various signal processing and filtration functions with regard to the acquired image signals, such as for initial adjustment of dynamic ranges, interleaving of digital image data, and so forth.

In the embodiment illustrated in FIG. 1, system controller 24 is coupled to a rotational subsystem 32 and a linear positioning subsystem 34. The rotational subsystem 32 enables the X-ray source 12, collimator 14 and the detector 22 to be rotated one or multiple turns around the subject 18. It should be noted that the rotational subsystem 32 might include a gantry. Thus, the system controller 24 may be utilized to operate the gantry. The linear positioning subsystem 34 enables the subject 18, or more specifically a table, to be displaced within an opening in the CT system 10. Thus, the table may be linearly moved within the gantry to generate images of particular areas of the subject 18. In the depicted embodiment, the system controller 24 controls the movement of the rotational subsystem 32 and/or the linear positioning subsystem 34 via a motor controller 36.

In general, system controller 24 commands operation of the imaging system 10 (such as via the operation of the source 12, detector 22, and positioning systems described above) to execute examination protocols and to process acquired data. For example, the system controller 24, via the systems and controllers noted above, may rotate a gantry supporting the source 12 and detector 22 about a subject of interest so that a plurality of radiographic views may be collected for processing. In the present context, system controller 24 also includes signal processing circuitry, typically based upon a general purpose or application-specific digital computer, associated memory circuitry for storing programs and routines executed by the computer (such as routines for executing image processing and reconstruction techniques described herein), as well as configuration parameters and image data, interface circuits, and so forth.

In the depicted embodiment, the image signals acquired and processed by the system controller 24 are provided to a processing component 30 for reconstruction of images. The processing component 30 may be one or more microprocessors and/or co-processors suitable for implementing projection, back-projection, and/or reconstruction algorithms as discussed herein. The one or more processors and/or co-processors may execute such algorithms in a parallel or non-parallel implementation. The data collected by the data acquisition system 28 may be transmitted to the processing component 30 directly or after storage in a memory 38. It should be understood that any type of memory capable of storing a large amount of data might be utilized by such an exemplary system 10. Moreover, the memory 38 may be located at the acquisition system site or may include remote components for storing data, processing parameters, and routines for iterative image reconstruction described below.

The processing component 30 is configured to receive commands and scanning parameters from an operator via an operator workstation 40 typically equipped with a keyboard and other input devices. An operator may control the system 10 via the input devices. Thus, the operator may observe the reconstructed images and/or otherwise operate the system 10 via the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. It should be noted that PACS 46 might be coupled to a remote client 48, radiology department information system (RIS), hospital information system (HIS) or to an internal or external network, so that others at different locations may gain access to the image, the image data, and optionally the variance data.

While the preceding discussion has treated the various exemplary components of the imaging system 10 separately, one of ordinary skill in the art will appreciate that these various components may be provided within a common platform or in interconnected platforms. For example, the processing component 30, memory 38, and operator workstation 40 may be provided collectively as a general or special purpose computer or workstation configured to operate in accordance with the present technique. Likewise, the system controller 24 may be provided as part of such a computer or workstation.

The projection algorithm implemented by the processing component 30 may be used for both forward projection (generating a sinogram from an image) and backward projection (generating an image from a sinogram). In selecting a suitable projection algorithm, one of ordinary skill in the art will appreciate that back projection and re-projection operations are important components of an iterative reconstruction algorithm. A suitable projection algorithm should, therefore, execute efficiently and minimize noise or high frequency artifacts to allow rapid iteration of the projection operations while providing suitable image quality.

Examples of projection methods include methods that are pixel-driven or ray-driven. Fundamentally both the pixel-driven and ray-driven algorithms re-sample the sinogram or image values as a function of detector elements or pixels (respectively). For example, pixel-driven back-projection projects a line through the center of the image pixel of interest onto the detector array using the imaging geometry. Once a location of intersection on the detector is determined, a value is obtained from the detector (such as by linear interpolation) and the result is accumulated in the image pixel. In such a back-projection approach, a sinogram row is the source signal and an image row is the destination signal. For each image row, the pixel centers are mapped on to the detector. Pixel-driven projection is the transpose operation of the back-projection operation described above. Pixel-driven techniques are so named because the index of the main processing loop is the image pixel index.

Conversely, ray-driven projection generally consists of approximating each ray-integral by weighting and summing all image pixels that lie close to the ideal projection line. The ideal projection line may be approximated by projecting a line through the image to the center of the detector element of interest using the imaging geometry. A location of intersection is calculated for each image row (or column), a value is obtained from the image row, such as by linear interpolation, and the result is accumulated in the detector element. In such a projection approach, an image row is the source signal and a sinogram row is the destination signal. For each image row, the detector element centers are mapped on to the image row. Ray-driven back-projection is the transpose operation of the projection operation described above. In ray-driven techniques the index of the main processing loop is the projection line index. While ray and projection-driven techniques have certain advantages, other projection methods may be as or more suitable in certain implementations.

For example, an alternative projection algorithm is a distance-driven projection algorithm. The distance-driven projection technique can be summarized as the mapping of pixel and detector coordinates onto a common line or axis followed by a kernel operation. Distance-driven techniques are based upon the recognition that each view (i.e., source) position defines a bijection between the position on the detector and the position within an image row or column. Therefore, every point within an image row or column is mapped uniquely onto a point on the detector and vice versa. A length of overlap between each image pixel and detector element may, therefore, be defined. This overlap may be calculated by mapping all pixel boundaries in an image row or column of interest onto the detector or by mapping all detector element boundaries of interest onto the centerline of the image or column row of interest. In one embodiment, this is accomplished by mapping both image pixel and detector element boundaries onto a common line or axis by connecting all pixel boundaries and all detector element boundaries with the source and calculating the intercepts on the common axis. Based on these calculated intercepts, the length of overlap between each image pixel and each detector element can be calculated as seen on the common axis. A one-dimensional kernel operation may then be applied to map data from one set of boundaries to the other. The normalized length of overlap between each image pixel and detector cell may be used to define the weight used in projection and back-projection processes. The distance driven projection algorithm is well suited for iterative reconstruction and can be efficiently implemented in hardware. The distance-driven projection algorithm performs both forward-projection and back projection operations without artifacts, has low arithmetic complexity, and provides for sequential memory accesses. In addition, the distance-driven projection algorithm is symmetric with regard to the forward-projection and back-projection operations performed, allowing hardware resource sharing in a hardware implementation. As will be appreciated by those skilled in the art, this symmetry is also necessary for the functioning of some iterative reconstruction algorithms (such as Conjugate Gradients).

As will be appreciated by those of ordinary skill in the art, selection of a suitable projection algorithm is only one aspect of implementing an iterative reconstruction algorithm in hardware. Another aspect of such an implementation is the selection of a cost function. Well-known cost functions include maximum-likelihood, maximum-a-posteriori, weighted least squares, and penalized weighted least squares. The latter is given by:

$$\sum_i w_i (\hat{p}_i^k - p_i)^2$$

where $w_i$ are the statistical weights for sinogram element I and p and p^ are the measured and calculated sinograms respectively. In one embodiment of the present technique, the quadratic term is replaced by a more general function, for example corresponding to a more heavily-tailed statistical distribution ξ. Correspondingly, the error sinogram in the first derivative of the cost function will undergo a non-linear transformation ξ'. For example, ξ(p) can be a q-Generalized Gaussian function or a Generalized Geman function. In another example a double sigmoid function may be applied to the error sinogram e(Δp):

$$e'(\Delta p) = e(\Delta p) \cdot s(\Delta p, \text{delta1}, \text{slope}) \cdot [1 - s(\Delta p, -\text{delta1}, \text{slope})]$$

where $$s(\Delta p, \text{delta}, \text{slope}) = 1/(1 + \exp(-\text{slope} \cdot (\Delta p - \text{delta})))$$

As will be appreciated by those of ordinary skill in the art, similar transformations can be designed in order to maximize image quality, minimize image noise, maximize spatial resolution, and minimize image artifacts due to inconsistent data.

Yet another aspect of such an implementation is the selection of a suitable iterative reconstruction algorithm. One such iterative reconstruction algorithm is the iterative coordinate descent (ICD) algorithm. The baseline ICD technique operates by iterating over image pixels. Each pixel iterates in the inner loop over its corresponding sinogram data track. A typical ICD updated step is given by:

$$\mu_j^k = \begin{cases} \mu_j^{k-1} + \delta_j^k & j = \phi(k) \\ \mu_j^{k-1} & j \neq \phi(k) \end{cases} \qquad \delta_\phi^k = \frac{\sum_i w_i l_{i\phi}(p_i - \hat{p}_i^{k-1})}{\sum_i w_i l_{i\phi}^2}$$

where j is the pixel index, k is the sub-iteration number, and ϕ(k) specifies which pixel is updated in sub-iteration k, μ is the pixel value, p and p^ are the measured and calculated sinogram values, w are the weights from the weighted least squares cost criterion, and $l_{i\phi}$ is the contribution from pixel ϕ to sinogram element i.

In an exemplary embodiment, ICD is implemented using pixel subsets, which provide good parallelizability and computational performance. In particular, updating all pixels in a subset independently allows the update algorithm to be implemented in parallel. Furthermore, use of pixel subsets allows projection and back-projection steps (as discussed herein) to be implemented simultaneously and provides more uniform image convergence. Exemplary logic for iteratively implementing the ICD algorithm using pixel subsets is provided in FIG. 2. In the depicted exemplary embodiment, an image estimate 50 (such as a direct reconstruction or filtered backprojection of the raw image data) is provided. In instances where the image estimate 50 is converged, the converged estimate may be output as a reconstructed image 52. In one embodiment, the image estimate 50 is considered converged when the desired spatial resolution for the reconstructed image 52 is reached. In one embodiment, the update step is then given by:

$$\mu_j^k = \begin{cases} \mu_j^{k-1} + \delta_j^k & j \in \Phi \\ \mu_j^{k-1} & j \notin \Phi. \end{cases}$$

where all the pixels belonging to subset Φ are updated simultaneously.

In one embodiment, pixel subsets are generated when the image estimate 50 is not converged and the ICD algorithm leverages the pixel subsets to accelerate image reconstruction. In one such embodiment, the image estimate 50 is divided into pixel subsets with each subset containing a number of pixels that are spatially separated, i.e., sparse or otherwise not neighboring. In other embodiments, however, the pixel subsets are selected such that each subset contains neighboring or proximate pixels, i.e., spatially localized "blocks" of pixels. The pixels in each subset can be processed concurrently, as described herein. In one embodiment, the pixel subsets are selected to minimize interactions of the respective sinogram tracks of the pixels within a subset. Every iteration of the exemplary technique consists of a number of sub-iterations. In each sub-iteration the pixels in one pixel subset are simultaneously and independently updated (comparable to a number of Jacobi updates).

The image estimate 50 is projected (block 56) to generate a calculated sinogram 58. In one embodiment, the projection is done using a distance-driven algorithm or any other suitable forward projector. An error sinogram 60 is derived (block 62) from the calculated sinogram 58. The error sinogram 60 may be generated by various techniques. For example, in an exemplary implementation, a measured sinogram 64 derived from the image data is subtracted from the calculated sinogram 58 to generate the error sinogram 60. In such an implementation, the image data from which the measured sinogram 64 is derived is typically log corrected and in line-integral attenuation form. In other embodiments, the derivation of the error sinogram 60 may be based upon a suitable statistical model, such as a Poisson or least squares model.

In one embodiment, the error sinogram 60 is sparse back-projected (block 68), such as via distance-driven back-projection or any other suitable back-projector, based on a current pixel subset. The sparse back-projection step 68 generates a sub-iteration image update 70, corresponding to the current pixel subset, that may be used to update (block 72) the current image estimate. For example, in one embodiment, the image estimate 50 may be updated by subtracting the sub-iteration image update 70. In addition, the sub-iteration image update 70 may be sparse projected (block 76) based on the current pixel subset to generate a sinogram update 78. The sinogram update 78 and error sinogram 60 may then be used to update (block 80) the error sinogram for the next pixel subset sub-iteration. The process depicted by FIG. 2 may be repeated for different pixel subsets and image estimates 50 until convergence occurs and a reconstructed image 52 is obtained. In one embodiment, the sparse distance-driven projection/backprojection is implemented similarly to the conventional distance-driven projection-backprojection, by modifying the loop over the pixel-/voxel-boundaries such that only the pixels belonging to the pixel subset of interest are addressed, while all interleaving pixels or image rows or columns that do not belong to the pixel subset of interest are skipped.

In another embodiment, the image update 70 may be multiplied by a scaling image 71 prior to subtraction from the image estimate 50. This scaling image 71 may be chosen to improve the convergence properties of the iterative reconstruction algorithm. For example, the scaling image 71 may be obtained by taking an image of all ones, projecting this image using the current pixel subset, multiplying the resulting sinogram by a weight sinogram that measures the relative confidence in each sinogram pixel, and then backprojecting the weighted sinogram onto the current pixel subset. The reciprocal of the resulting image can then be used as a scaling image 71 to be multiplied by the image update 70 prior to subtracting it from image estimate 50.

While the above discussion relates to the processing of pixel subsets where the pixels in a subset are spatially separated, other types of pixel subsets may be employed in conjunction with ICD techniques. For example, in one embodiment, the pixel subsets that are simultaneously processed are block-based, i.e., neighboring or otherwise not spatially separated. In one implementation, each iteration of the ICD algorithm includes multiple sub-iterations and each sub-iteration simultaneously updates a different subset or block of neighboring or proximate pixels via an n×n inversion. For example, in one embodiment, a block of adjacent pixels are updated by a direct inversion technique, such as by inverting the Hessian:

$$x_j = A_{\phi,j}^{-1} y_\phi$$

where $$y_\phi = \left[ \sum_i w_i l_{i\phi} (p_i - \hat{p}_i^{k-1}) \right]$$

$$A_{\phi,j} = \left[ \sum_i w_i l_{ij} l_{i\phi} \right]$$

$$x_j = [\delta_j^k].$$

In this embodiment, this process is repeated for all the blocks (or pixel subsets) and for all iterations.

Figure 3:
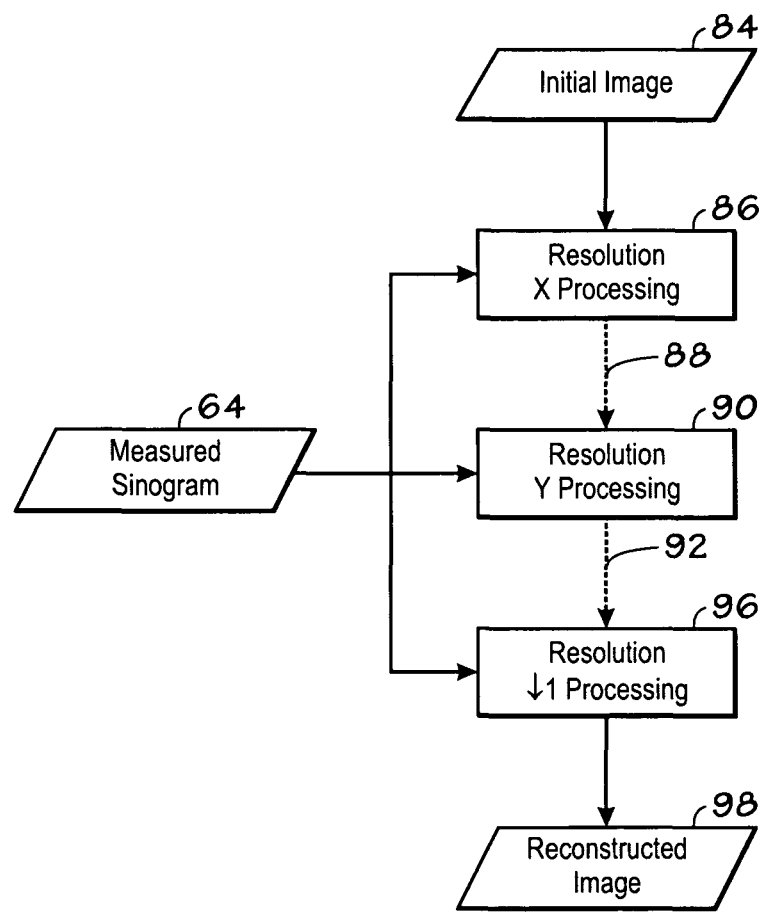
FIG. 3 is a flowchart depicting exemplary logic for implementing a portion of another iterative coordinate descent reconstruction algorithm, in accordance with the present technique.
Figure 4:
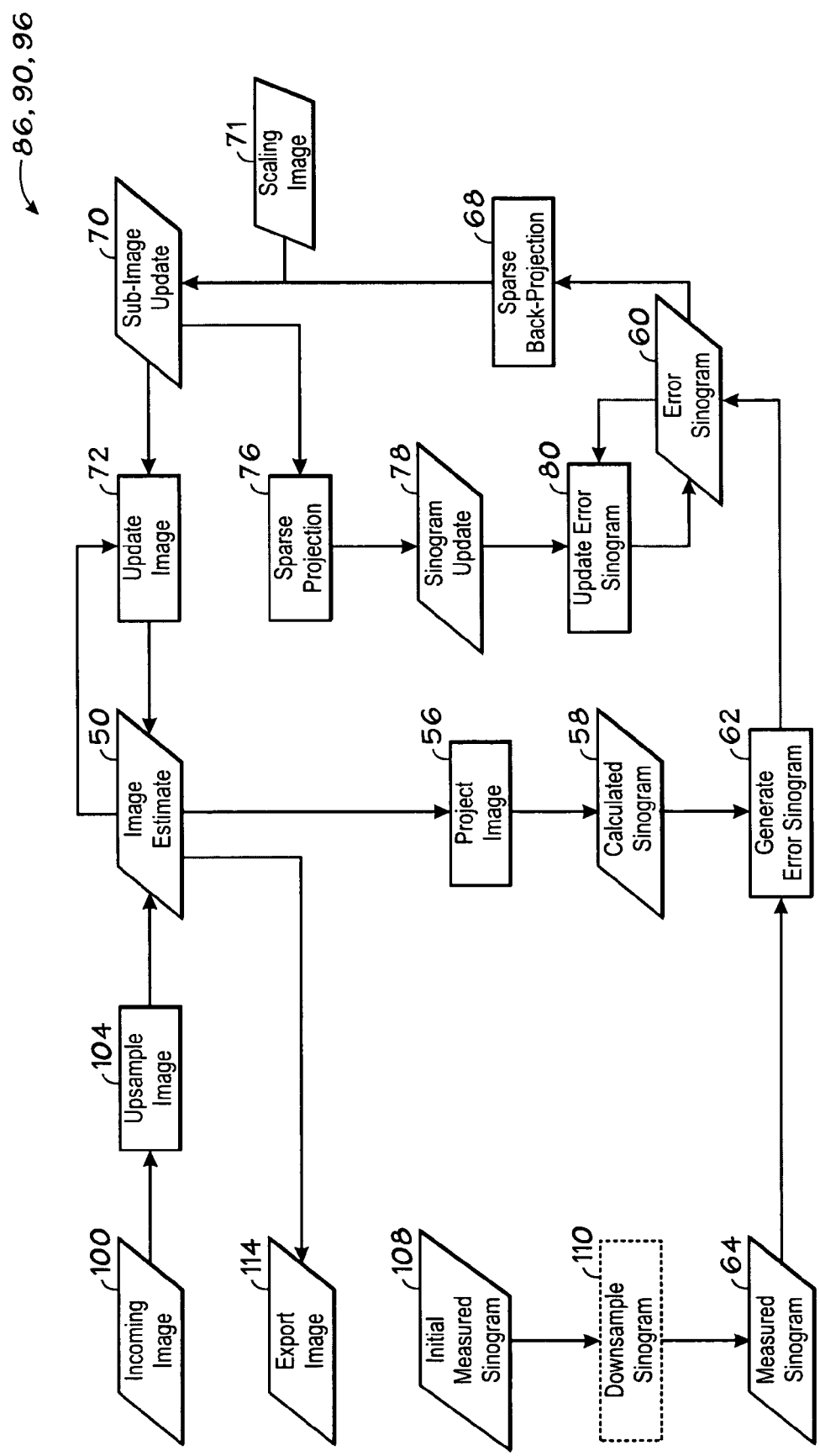
FIG. 4 is a flowchart depicting exemplary logic for implementing another portion of the iterative coordinate descent reconstruction algorithm of FIG. 3.

Furthermore, in an exemplary least squares approach, the use of pixel subsets may be combined with multi-resolution processing, as depicted in FIGS. 3 and 4, to improve convergence properties. In such an embodiment, an iteration performed at a lower resolution may generate an image which is then processed at a higher resolution, and so forth, until an image of the desired resolution is generated. For example, referring now to FIG. 3, an initial image estimate 84 may be processed at a first resolution (block 86) using pixel subsets and ICD techniques and based upon a measured sinogram 64. The output 88 of the processing may be the input for a subsequent processing step at a higher resolution and so forth. Intermediate resolution processing steps (block 90) likewise employ pixel subsets and ICD processing techniques along with measured sinogram data 64 to generate additional outputs 92 for subsequent processing. At the highest resolution processing step (block 96) the output of the preceding iteration is the input for the ICD iteration, along with the measured sinogram data 64). The output of the highest resolution processing step (block 96) is the reconstructed image 98, which may be displayed or otherwise provided to a clinician for review or analysis.

Referring now to FIG. 4, the iterated processing steps 86, 90, 96 are described in greater detail. In this depiction, an incoming image 100 is provided. The incoming image 100 may be the initial image, such as an image generated as a filtered backprojection of the original image data, for the first iteration, or may be the output of a preceding iteration. Where the incoming image 100 is an output of a preceding processing iteration, the incoming image may be upsampled (block 104) to the next higher resolution of interest, thereby generating the image estimate 50. Upsampling may not occur however, where the incoming image 100 is not the output of a preceding iteration step, such as during the initial iteration. In an alternate embodiment, the incoming image 100 may be of a lower resolution (e.g., a low resolution filtered backprojection reconstruction), and may require upsampling prior to its use as the initial image in the iterative reconstruction. Generally, iterations can be performed at one or more different spatial resolutions, switching from lower to higher (or vice versa) spatial resolution by performing up-sampling (or down-sampling) as appropriate.

Figure 2:
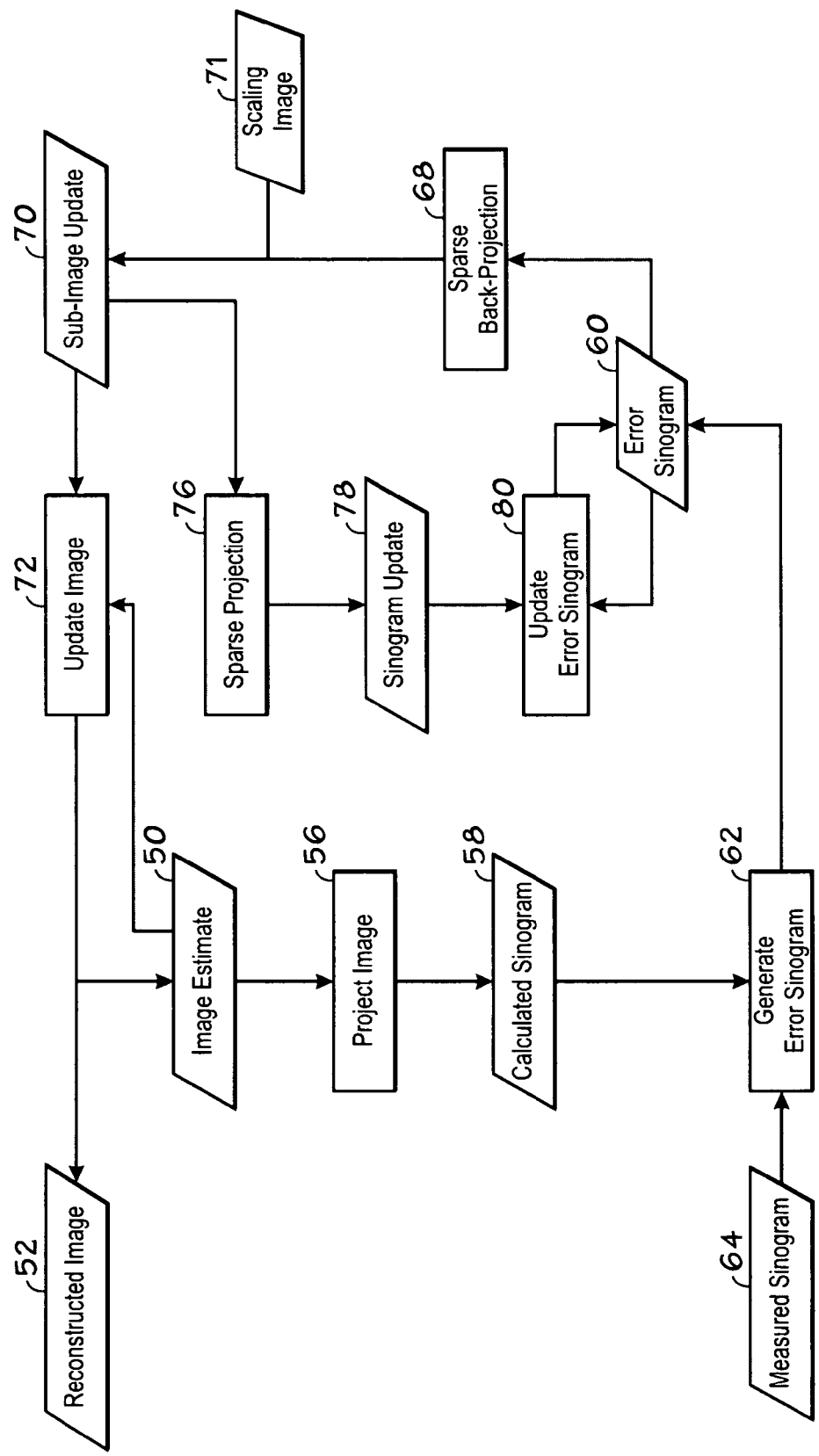
FIG. 2 is a flowchart depicting exemplary logic for implementing an iterative coordinate descent reconstruction algorithm, in accordance with the present technique.

As discussed with regard to FIG. 2, the image estimate 50 is divided into pixel subsets and the image estimate 50 is projected (block 56) to generate a calculated sinogram 58. An error sinogram 60 is derived (block 62) from the calculated sinogram 58. The error sinogram 60 may be generated by various techniques. In implementations employing a measured sinogram 64 derived from the projection data, the measured sinogram 64 may be derived from an initial measured sinogram 108, which is downsampled (block 110), when appropriate, to correspond to the resolution of the current iteration. In such an embodiment, the measured sinogram 64 may be subtracted from the calculated sinogram 58 to generate the error sinogram 60. In such an implementation, the image data from which the measured sinogram 64 is derived is typically log corrected and in line-integral attenuation form. In other embodiments, the derivation of the error sinogram 60 may be based upon a suitable statistical model, such as a Poisson or least squares model.

In the depicted embodiment, the error sinogram 60 is sparse back-projected (block 68) based on the current pixel subset, as discussed with regard to FIG. 2. The sparse back-projection step 68 generates a sub-iteration image update 70, corresponding to the current pixel subset, that may be used to update (block 72) the current image estimate. The updated image estimate may undergo further processing or, if all sub-iterations of the iteration are complete, may be exported as an export image 114. If additional iterations remain, the export image 114 may be the incoming image 100 for the next iteration. In no iterations remain, the export image 114 is the reconstructed image 98.

The sub-iteration image update 70 may also be sparse projected (block 76) based on the current pixel subset to generate a sinogram update 78. The sinogram update 78 and error sinogram 60 may then be used to update (block 80) the error sinogram for the next pixel subset sub-iteration, as described with regard to FIG. 2.

For example, in an exemplary embodiment, if the reconstructed image 98 is to be a 512×512 pixel image, a three iteration schedule may be employed. The first iteration may comprise a 128×128 pixel image which is processed using 4×4 pixel subsets, each subset consisting of 32×32 pixels, and $2^n$ (here $2^4$) iterations. The output of the processing at the first resolution may be upsampled to form a 256×256 pixel image which is processed using 8×8 pixel subsets, each subset consisting of 32×32 pixels, and 22 iterations. The output of the processing at the second resolution may be upsampled to form a 512×512 pixel image which is processed using 16×16 pixel subsets, each subset consisting of 64×64 pixels, and 21 iterations. As one of ordinary skill in the art will appreciate, resolutions, iterations for each resolution, number of pixels per subset, relaxation factor, and so forth are all factors that may be adjusted to achieve the desired computational and image quality properties.

In a further embodiment of the present techniques, in order to improve convergence, at every sub-iteration corresponding to a certain pixel subset (whether neighboring or spatially separated), an update image is calculated and applied to the pixels in the subset, as described above. Likewise, as described above, the equivalent update to the error sinogram is calculated and applied to the sinogram. In addition, the equivalent update to the cost function is calculated. After a desired number of sub-iterations (possibly every sub-iteration), an optimal linear combination of the last N updates is calculated that most nearly achieves the desired sinogram or cost function, i.e., the linear combination is calculated which minimizes the average error between the measured and calculated error sinograms.

For example, in one embodiment, in every sub-iteration, k, the pixel values, $\mu_j$, are incremented by $\delta_j^k$, which is zero for all the pixels j that do not belong to the subset $\Phi(k)$. After a user-defined number of iterations or sub-iterations, a number of previous updates $\delta_j^k$ are linearly combined in order to achieve faster convergence as given by the exemplary equation:

$$\mu_j^{new} = \mu_j + c_1 \cdot \delta_j^k + c_2 \cdot \delta_j^{k+1} + c_3 \cdot \delta_j^{k+2} + c_4 \cdot \delta_j^{k+3} + \ldots + c_N \cdot \delta_j^{k+N}$$

where $c_1, c_2, \ldots c_N$ are optimized by solving:

$$\mathrm{argmax}(\mu_j^{new})$$

This optimization technique is known outside the area of image reconstruction as Krylov subspace optimization.

While in the present discussion reference is made to a CT scanning system in which a source and detector rotate on a gantry arrangement, it should be borne in mind that the present technique is not limited to data collected on any particular type of scanner. For example, the technique may be applied to data collected via a scanner in which an X-ray source and/or a detector are effectively stationary and an object is rotated, or in which the detector is stationary but an X-ray source rotates. Further, the data could originate in a scanner in which both the X-ray source and detector are stationary, as where the X-ray source is distributed and can generate X-rays at different locations. Further, the present technique could apply to three-dimensional or cone beam acquisitions as well as to two-dimensional acquisitions. Hence any reference to the word pixel should be understood as also encompassing a voxel in such three-dimensional contexts. In brief, it should be borne in mind that the system of FIG. 1 is described herein as exemplary an system only. Other system configurations and operational principles may, of course, be envisaged for acquiring and processing image data and variance data and for utilizing the data as discussed below. Furthermore, the techniques described herein may be applied to various other iterative tomographic reconstructions, such as those associated with positron emission tomography (PET) and single positron emission computed tomography (SPECT), in addition to CT. The techniques described herein may also be used in tomosynthesis reconstructions, where only a small number of view angles or a limited angular range of data are available. For example, the techniques discussed herein may be employed with penalized or unpenalized and/or weighted or unweighted least-squares iterative tomographic reconstruction techniques.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for processing image data, comprising the steps of:
   providing an image comprising two or more subsets of pixels; and
   directly inverting a respective Hessian matrix corresponding to each subset of pixels such that the pixels of each subset are simultaneously optimized with regard to a cost function.

2. The method of claim 1, wherein the act of directly inverting a respective Hessian matrix corresponding to each subset of pixels is iteratively performed.

3. The method of claim 2, wherein the subsets of pixels are modified between iterations such that the pixel composition of the subsets is different each iteration.

4. The method of claim 2, wherein the subsets of pixels are modified between iterations such that the pixel size of the subsets is different each iteration.

5. The method of claim 1, wherein the image comprises a medical diagnostic image.

6. The method of claim 1, wherein the cost function corresponds to at least one of a maximum-likelihood function, a maximum-a-posteriori function, a weighted least squares function, and a penalized weighted least squares function.

7. The method of claim 1, wherein each subset of pixels comprises substantially proximate pixels.

8. The method of claim 1, wherein each subset of pixels comprises substantially spatially separated pixels.

9. One or more non-transitory computer-readable media encoded with a computer program, the computer program configured to execute the steps of:
   providing an image comprising two or more subsets of pixels; and
   directly inverting a respective Hessian matrix corresponding to each subset of pixels such that the pixels of each subset are simultaneously optimized with regard to a cost function.

10. The one or more computer-readable media of claim 9, wherein the computer program is configured to iteratively execute the step of directly inverting the respective Hessian matrix.

11. The one or more computer-readable media of claim 10, wherein the subsets of pixels are modified between iterations such that the pixel composition of the subsets is different each iteration.

12. The one or more computer-readable media of claim 10, wherein the subsets of pixels are modified between iterations such that the pixel size of the subsets is different each iteration.

13. The one or more computer-readable media of claim 9, wherein the cost function corresponds to at least one of a maximum-likelihood function, a maximum-a-posteriori function, a weighted least squares function, and a penalized weighted least squares function.

14. The one or more computer-readable media of claim 9, wherein each subset of pixels comprises substantially proximate pixels.

15. The one or more computer-readable media of claim 9, wherein each subset of pixels comprises substantially spatially separated pixels.

16. A tomographic imaging system, comprising:
   a processing component configured to provide an image comprising two or more subsets of pixels, and to directly invert a respective Hessian matrix corresponding to each subset of pixels such that the pixels of each subset are simultaneously optimized with regard to a cost function.

17. The tomographic imaging system of claim 16, wherein the processing component is further configured to directly invert the respective Hessian matrix iteratively.

18. The tomographic imaging system of claim 17, wherein the subsets of pixels are modified between iterations such that the pixel composition of the subsets is different each iteration.

19. The tomographic imaging system of claim 17, wherein the subsets of pixels are modified between iterations such that the pixel size of the subsets is different each iteration.

20. The tomographic imaging system of claim 16, wherein the cost function corresponds to at least one of a maximum-likelihood function, a maximum-a-posteriori function, a weighted least squares function, and a penalized weighted least squares function.

21. The tomographic imaging system of claim 16, wherein each subset of pixels comprises substantially proximate pixels.

22. The tomographic imaging system of claim 16, wherein each subset of pixels comprises substantially spatially separated pixels.

* * * * *